(12) United States Patent
Okamoto et al.

(10) Patent No.: US 8,980,124 B2
(45) Date of Patent: Mar. 17, 2015

(54) AROMATIC COMPOUND GELLING AGENT HAVING PERFLUOROALKYL GROUP

(75) Inventors: Hiroaki Okamoto, Ube (JP); Yuki Morita, Ube (JP)

(73) Assignee: National University Corporation Yamaguchi University, Yamaguchi-Shi (JP)

( * ) Notice: Subject to any disclaimer, the term of this patent is extended or adjusted under 35 U.S.C. 154(b) by 1064 days.

(21) Appl. No.: 12/087,998

(22) PCT Filed: Jan. 19, 2007

(86) PCT No.: PCT/JP2007/051216
§ 371 (c)(1),
(2), (4) Date: Jul. 18, 2008

(87) PCT Pub. No.: WO2007/083843
PCT Pub. Date: Jul. 26, 2007

(65) Prior Publication Data
US 2009/0090891 A1 Apr. 9, 2009

(30) Foreign Application Priority Data

Jan. 20, 2006 (JP) ................. 2006-012697
Jan. 20, 2006 (JP) ................. 2006-012702
Jan. 23, 2006 (JP) ................. 2006-013526

(51) Int. Cl.
| | | |
|---|---|---|
| H01M 4/88 | (2006.01) |
| C07C 381/00 | (2006.01) |
| C07C 41/00 | (2006.01) |
| C07C 41/24 | (2006.01) |
| C07C 41/16 | (2006.01) |
| C07C 41/26 | (2006.01) |
| C07C 41/30 | (2006.01) |
| C07C 43/225 | (2006.01) |
| C07C 43/23 | (2006.01) |
| C07C 323/20 | (2006.01) |
| H01M 10/0525 | (2010.01) |
| H01M 10/0565 | (2010.01) |

(52) U.S. Cl.
CPC ............. *C07C 41/24* (2013.01); *C07C 41/16* (2013.01); *C07C 41/26* (2013.01); *C07C 41/30* (2013.01); *C07C 43/225* (2013.01); *C07C 43/23* (2013.01); *C07C 323/20* (2013.01); *H01M 10/0525* (2013.01); *H01M 10/0565* (2013.01); *H01M 2300/0085* (2013.01); *Y02E 60/122* (2013.01)

USPC ............. 252/182.1; 568/49; 568/54; 568/631

(58) Field of Classification Search
USPC ........ 429/300, 303, 309, 314; 252/62.2, 18.2, 252/182.1; 568/49, 54, 631
See application file for complete search history.

(56) References Cited

U.S. PATENT DOCUMENTS

| | | | |
|---|---|---|---|
| 6,114,068 A * | 9/2000 | Yamada et al. | 429/300 |
| 6,239,077 B1 | 5/2001 | Andoh et al. | |
| 7,351,452 B2 * | 4/2008 | Goodby et al. | 428/1.1 |
| 2004/0073054 A1 | 4/2004 | Zhang et al. | |
| 2006/0008678 A1 | 1/2006 | Fukushima et al. | |
| 2006/0222865 A1 * | 10/2006 | Hoshino et al. | 428/446 |

FOREIGN PATENT DOCUMENTS

| | | |
|---|---|---|
| EP | 1445251 A1 | 8/2004 |
| GB | 2415959 A | 1/2006 |
| JP | 6-220182 A | 8/1994 |
| WO | WO-2004/007407 A2 | 1/2004 |
| WO | WO 2005/054256 A1 | 6/2005 |

OTHER PUBLICATIONS

Johansson et al., Fluorophobic effect generates a systematic approach to the synthesis of the simplest class of rodlike liquid crystals containing a single benzene unit, chem. mater. 1997,9, 164-175.*
Robert J. Twieg et al.; Observations of a "Gel" Phase in Binary Mixtures of Semifluorinated . . . ; Macromolecules, 1985, No. 18, pp. 1361-1362.
Mathew George et al.; N-Alkyl Perfluoroalkanamides . . . ; J. Am. Chem. Soc. 2003, No. 125. pp. 10275-10283.
Extended European Search Report dated Mar. 24, 2010, for European Application No. 07707448.2.
Morita et al., "Gelation of 1-Alkoxy-4-(2-Perfluoroalkyl)Ethoxybenzenes in Organic Solvents", *Molecular Crystals and Liquid Crystals*, vol. 435, Jun. 1, 2005, pp. 813-822, XP008119184.

* cited by examiner

*Primary Examiner* — Monique Peets
(74) *Attorney, Agent, or Firm* — Birch, Stewart, Kolasch & Birch, LLP

(57) ABSTRACT

Aromatic compounds having a perfluoroalkyl group and a gelling agent for gelling an organic liquid which is composed of any one of them. This gelling agent can gel many kinds of organic liquids by adding a small amount thereof.

9 Claims, No Drawings

AROMATIC COMPOUND GELLING AGENT HAVING PERFLUOROALKYL GROUP

TECHNICAL FIELD

The present invention relates to a novel gelling agent for organic liquids, comprising a perfluoroalkyl derivative as an effective component and an organic liquid gel formed by gelling with this gelling agent. The organic liquid gel of the present invention can be used as a gel electrolyte.

BACKGROUND ART

Although the electrolyte of a lithium ion battery is generally liquid, a gel or solid electrolyte may be used as a polymer electrolyte. The following characteristic properties are required for all of these electrolytes.
1) They must exhibit high conductivity (high movability of a lithium ion).
2) They must exhibit great chemical and electrochemical stability for electrode materials.
3) They must have a wide usable temperature range.
4) They must have high safety.
5) They must be inexpensive.

An aprotic organic solvent having high specific dielectric constant and low viscosity is suitable as an electrolyte solvent for obtaining high conductivity, which contains a lithium salt in a high concentration. However, since a solvent having high specific dielectric constant and strong polarity has high viscosity, a mixture of solvents is used in an actual electrolyte. For example, there is known a mixed solvent of propylene carbonate (PC) having a dielectric constant of 64.4 and a viscosity of 2.3 cp or ethylene carbonate (EC) having a dielectric constant of 95.3 and a viscosity of 1.9 cp and dimethyl carbonate (DMC) having a viscosity of 0.59 cp. This mixed solvent has composition which shows maximum conductivity, and this composition is investigated in detail together with the type of an electrolyte salt to be added.

As the electrolyte salt are used lithium perchlorate ($LiClO_4$), and $LiPF_6$, $LiAsF_6$, $Li(CF_3SO_2)_2N$, $LiBF_4$ and $LiCF_3SO_3$ all of which contain fluorine. The ion conductivity of an organic solvent electrolyte obtained by dissolving one of these electrolyte salts is about $10^{-2}$ S/cm.

A gel electrolyte which is a mixture of an organic polymer and a liquid electrolyte has high ion conductivity and was commercialized earlier than a solid electrolyte. A carbon-based negative-electrode material is used in the gel electrolyte to manufacture a lithium ion secondary battery, especially a thin film battery.

Heretofore, a low-molecular weight gelling agent or a polymer gelling agent has been used to solidify organic liquids such as animal and vegetable oils, esters, polyols, ethers, alcohols and hydrocarbons in industrial processing fields such as coating compositions, inks, lubricant oils, agricultural products, marine products, cosmetics, medical goods, fibers, resins, polymers, rubbers and metals. The polymer gelling agent is often used in the technical field of batteries as a gelling agent for gel electrolytes.

The low-molecular weight gelling agent was developed after the above polymer gelling agent, and 12-hydroxystearic acid, dialkylurea derivatives and dibenzylidene sorbitol are known as the low-molecular weight gelling agent.

Although 12-hydroxystearic acid out of these is inexpensive, the number of kinds of organic liquids which can be gelled by this is small, and the softening temperature of the obtained gel is low. The number of kinds of organic liquids which can be gelled by dialkylurea derivatives is also small. Although a strong gel is formed by the addition of a small amount of dibenzylidene sorbitol, it has a defect that it liberates benzaldehyde and is not suitable for solidifying a short-chain alcohol having a low boiling point because it has a high melting point. Alkali metal salts and alkali earth metal salts of a fatty acid must be added in large quantities for gelation or solidification and their usable conditions are limited.

It has been reported that a perfluoroalkylalkane represented by the formula $F(CF_2)_n(CH_2)_nH$ in which n is 12 and m is 8 to 20 gels decane and that a perfluoroalkylalkane of the above formula in which n is 10 and m is 12 gels a hydrocarbon solvent (refer to Robert J. Twang, et al, "Observations of a "Gel" Phase in Binary Mixtures of Semifluorinated n-Alkanes with Hydrocarbon Liquids" Macromolecules 1985, 18, 1361-1362).

It has also been reported that a perfluoroalkylalkane represented by the formula $F(CF_2)_8(CH_2)_8H$ gels methyl alcohol, ethyl alcohol and propyl alcohol (refer to Massimo Napoli, et al, "Synthesis of $F(CF_2)_8(CH_2)_8H$ and gel phase formation from its solutions in homologous alcohols).

However, since the kinds of organic liquids which can be gelled by the above prior art gelling agents are limited, a large amount of each of the gelling agents is required for gelation, an organic low-molecular weight gelling agent which can gel many kinds of organic liquids with a small amount has been unknown up till now. An organic low-molecular weight gelling agent which gels a high-dielectric constant solvent suitable for organic electrolytes has been unknown as well.

DISCLOSURE OF THE INVENTION

It is an object of the present invention to provide an aromatic compound having a perfluoroalkyl group which can gel many kinds of organic liquids and is advantageously used as an organic low-molecular weight gelling agent capable of gelling with a small amount and a manufacturing process thereof.

It is another object of the present invention to provide an organic low-molecular weight gelling agent which can gel a high-dielectric constant solvent suitable for organic electrolytes.

It is still another object of the present invention to provide a gel obtained by gelling an organic liquid with this organic low-molecular weight compound.

It is a further object and advantage of the present invention to provide a flame retardant gel.

Other objects and advantages of the present invention will become apparent from the following description.

According to the present invention, firstly, the above objects and advantages of the present invention are attained by an aromatic compound having a perfluoroalkyl group, represented by the following formulas (1), (2) or (3):

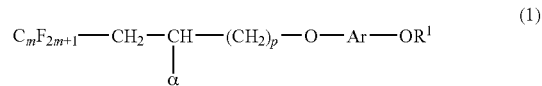

wherein α is a hydrogen atom or hydroxyl group, Ar is a substituted or unsubstituted divalent aromatic group having 5 to 30 aromatic nuclear atoms, $R^1$ is a saturated or unsaturated monovalent hydrocarbon group having 1 to 20 carbon atoms, m is a natural number of 6 to 12, and p is a natural number of 1 to 4, $$C_mF_{2m+1}-(CH_2)_q-Z-Ar-O \diagdown_{R^2} \atop C_mF_{2m+1}-(CH_2)_q-Z-Ar-O \diagup \qquad (2)$$

wherein $R^2$ is a saturated or unsaturated divalent hydrocarbon group having 2 to 20 carbon atoms, Ar and m are as defined hereinabove, Z is a sulfur atom or oxygen atom, and q is 0 or an integer of 1 to 4, $$C_mF_{2m+1}-(CH_2)_q-S-Ar-OR^1 \qquad (3)$$

wherein Ar, $R^1$, m and q are as defined hereinabove.

According to the present invention, secondly, the above objects and advantages of the present invention are attained by a process of manufacturing an aromatic compound having a perfluoroalkyl group, represented by the above formula (1), comprising the steps of:

1) reacting an aromatic compound represented by the following formula (4):

$$HO-Ar-OR^1 \qquad (4)$$

wherein Ar and $R^1$ are as defined in the above formula (1), with a halogenated alkene represented by the following formula (5):

$$CH_2=CH-(CH_2)_p-X^1 \qquad (5)$$

wherein p is as defined in the above formula (1), and $X^1$ is a halogen atom reactive to a hydroxyl group;

2) reacting the obtained product with a perfluoroalkyl iodide represented by the following formula (6):

$$C_mF_{2m+1}-I \qquad (6)$$

wherein m is as defined in the above formula (1); and 3) converting the iodine atom of the obtained product represented by the following formula (7) into a hydrogen atom or hydroxyl group:

$$C_mF_{2m+1}-CH_2-\underset{I}{CH}-(CH_2)_p-O-Ar-OR^1 \qquad (7)$$

wherein Ar, $R^1$, m and p are as defined in the above formula (1).

According to the present invention, thirdly, the above objects and advantages of the present invention are attained by a process of manufacturing an aromatic compound having a perfluoroalkyl group, represented by the above formula (2), comprising the steps of:

1) reacting an aromatic compound represented by the following formula (8):

$$HO-Ar-ZH \qquad (8)$$

wherein Ar and Z are as defined in the above formula (2), with a halogenated compound having a perfluoroalkyl group, represented by the following formula (9):

$$C_mF_{2m+1}-(CH_2)_q-X^2 \qquad (9)$$

wherein m and q are as defined in the above formula (2), and $X^2$ is a halogen atom reactive to a thiol group or hydroxyl group;

2) reacting the obtained product with a hydroxyl compound having a perfluoroalkyl group, represented by the following formula (10):

$$C_mF_{2m+1}-(CH_2)_q-Z-Ar-OH \qquad (10)$$

wherein Z, Ar, m and q are as defined in the above formula (2); and 3) reacting the obtained product with a dihalogenated hydrocarbon represented by the following formula (11):

$$X^2-R^2-X^2 \qquad (11)$$

wherein $R^2$ is as defined in the above formula (2), and $X^2$ is as defined in the above formula (9).

According to the present invention, in the fourth place, the above objects and advantages of the present invention are attained by a process of manufacturing an aromatic compound having a perfluoroalkyl group, represented by the above formula (3), comprising the steps of:

1) reacting an aromatic compound represented by the following formula (12):

$$HO-Ar-SH \qquad (12)$$

wherein Ar is as defined in the above formula (3), with a halogenated compound having a perfluoroalkyl group, represented by the above formula (9); and 2) reacting the obtained product with a halogenated hydrocarbon represented by the following formula (14):

$$R^1-X^1 \qquad (14)$$

wherein $R^1$ is as defined in the above formula (3), and $X^1$ is as defined in the above formula (5).

According to the present invention, in the fifth place, the above objects and advantages of the present invention are attained by a gelling agent for gelling an organic liquid, which comprises the aromatic compound having a perfluoroalkyl group of the present invention.

According to the present invention, in the sixth place, the above objects and advantages of the present invention are attained by use of the aromatic compounds having a perfluoroalkyl group of the present invention as gelling agents for gelling an organic liquid.

According to the present invention, finally, the above objects and advantages of the present invention are attained by a gel obtained by gelling an organic liquid with the gelling agent of the present invention.

BEST MODE FOR CARRYING OUT THE INVENTION

A description is first given of an aromatic compound having a perfluoroalkyl group, represented by the above formula (1) (to be referred to as "aromatic compound (1)" hereinafter), a manufacturing process thereof and use of the aromatic compound as a gelling agent.

The aromatic compound (1) of the present invention is represented by the following formula (1).

$$C_mF_{2m+1}-CH_2-\underset{\alpha}{CH}-(CH_2)_p-O-Ar-OR^1 \qquad (1)$$

In the above formula, $\alpha$ is a hydrogen atom or hydroxyl group, Ar is a substituted or unsubstituted divalent aromatic group having 5 to 30 aromatic nuclear atoms, $R^1$ is a saturated or unsaturated monovalent hydrocarbon group having 1 to 20 carbon atoms, m is a natural number of 6 to 12, and p is a natural number of 1 to 4.

In the formula (1), the aromatic group Ar is a divalent group of a cyclic compound which exhibits so-called "aromatic property". This cyclic compound may be either a carbon cyclic compound or a heterocyclic compound. These cyclic compounds may or may not be substituted by a substituent.

When the aromatic group Ar is a group of an aromatic carbon cyclic compound, it has 6 to 30 nuclear atoms and may or may not be substituted by a substituent. Examples of the aromatic carbon cyclic compound include compounds having a nucleus such as a phenylene group, biphenylene group, terphenylene group, naphthylene group, anthranylene group, phenanthrylene group, pyrenylene group, chrysenylene group or fluoranthenylene group.

When it is a group of an aromatic heterocyclic compound, it has 5 to 30 nuclear atoms. Examples of the compound include compounds having a nucleus such as a pyrrolene group, furanylene group, thiophenylene group, triazolene group, oxadiazolene group, pyridylene group or pyrimidylene group.

Out of these, the aromatic group Ar is preferably phenylene group, biphenylene group or naphthylene group.

Examples of the substituent for the aromatic nucleus include alkyl groups such as methyl group and ethyl group, and halogen atoms.

In the formula (1), the perfluoroalkyl group $C_mF_{2m+1}$ is a perfluoroalkyl group whose number "m" of carbon atoms is 6 to 12. A compound whose number "m" of carbon atoms is 5 or less has low gelation ability. A compound whose number "m" of carbon atoms is 13 or more is not molten by heating, depending on the type of an organic solvent.

Oligomethylene Group

In the formula (1), the number of carbon atoms of the oligomethylene group $(CH_2)_p$ is 1 to 4. A compound having the oligomethylene group $(CH_2)_p$ with 5 or more carbon atoms has low gelation ability.

In the formula (1), the hydrocarbon group $R^1$ is a saturated or unsaturated monovalent hydrocarbon group having 1 to 20 carbon atoms. The hydrocarbon group $R^1$ may be branched or not branched in the case of an aliphatic hydrocarbon. When it contains an aromatic hydrocarbon, a substituent may be existent in the aromatic nucleus. As a matter of course, it may be an arylalkyl group such as benzyl group.

A compound having no hydrocarbon group $R^1$ does not dissolve in an organic liquid and cannot gel an organic liquid. It is difficult to acquire raw materials when the number of carbon atoms is 21 or more.

For the manufacture of the above aromatic compound (1), an aromatic compound having a hydroxyl group and a hydrocarbon oxy group, represented by the following formula (4) is reacted with a halogenated alkene represented by the following formula (5), and further the obtained product is reacted with a perfluoroalkyl iodide represented by the following formula (6) to produce a compound represented by the following formula (7).

(4)

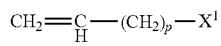
(5)

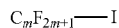
(6)

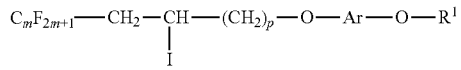
(7)

(the symbols in the above formulas are as defined in the above formula (1), and $X^1$ is a halogen atom reactive to a hydroxyl group (OH of the formula (4)), such as chlorine atom, bromine atom, iodine atom or fluorine atom.)

A compound represented by the following formula (1)-1 is obtained by dissolving the compound of this formula (7) in an organic solvent such as diethyl ether or THF and processing the resulting solution at normal temperature in the presence of a basic reagent such as lithium aluminum hydride.

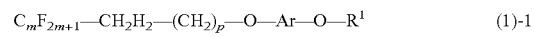
(1)-1

(the symbols in the above formula are as defined in the above formula (1).)

A compound represented by the following formula (1)-2 is obtained by processing the product of the above formula (7) with a basic reagent in the presence of a trace amount of water, preferably an equimolar amount to 10 times the molar amount of the compound of the formula (7) of water.

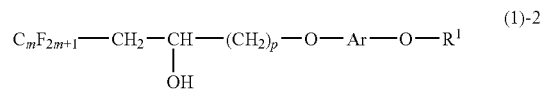
(1)-2

(the symbols in the above formula are as defined in the above formula (1).)

In the above two reactions, as it is very difficult to prevent water from being existent in a reaction system even when the compound of the formula (1)-1 is to be obtained, the compound of the formula (1)-2 is by-produced in most cases.

On the contrary, when the compound of the formula (1)-2 is to be obtained and a large amount of water is existent, hydrolysis occurs and the product of interest is not obtained. When the amount of water is too small, the compound of the formula (1)-1 is by-produced.

In general, by using a solvent containing water to such an extent that it naturally absorbs water in the air, a mixed gelling agent composed of the compounds of the formulas (1)-1 and (1)-2 can be obtained.

Almost all kinds of organic liquids can be gelled by adding 5 wt % or less of the gelling agent of the present invention which is composed of the above aromatic compound (1). Gelation occurs by adding the gelling agent of the present invention to an organic solvent, increasing the temperature to dissolve the gelling agent in the solvent and returning the resulting solution to normal temperature. The gelling agent of the present invention can gel a high-dielectric constant solvent suitable for organic hydrolytes, such as propylene carbonate. A gel formed by gelling a high-dielectric constant solvent with the gelling agent of the present invention can be used as an electrolyte gel. This electrolyte gel may be used in a lithium ion battery. It may also be used as an electrolyte gel for dye sensitization solar cells. The gelling agent of the present invention or a gel formed by using this may be used in industrial fields including processing fields such as coating compositions, inks, lubricant oils, agricultural products, marine products, cosmetics, medical goods, fibers, resins, polymers, rubbers and metals in addition to electrolyte for batteries.

To obtain an electrolyte gel, it is generally preferred that an ionic substance soluble in an organic liquid, for example, $LiClO_4$, $LiPF_6$, $LiAsF_6$, $Li(CF_3SO_2)_2N$, $LiBF_4$ or $LiCF_3SO_3$ in the case of a lithium ion battery should be dissolved in an organic solvent and the gelling agent of the present invention should be added to the resulting solution to produce a gel. As a matter of course, organic ionic liquids such as N,N,N-trialkyl(alkoxyalkyl)ammonium bis(trifluoromethanesulfonyl)imide and a mixture thereof dissolved in a nonionic organic solvent may be preferably used.

As described above, the gelling agent of the present invention can gel many kinds of organic liquids by adding a small amount thereof. The gelling agent of the present invention can gel a high-dielectric constant solvent suitable for organic electrolytes. Since a gel formed by gelling a high-dielectric constant solvent with the gelling agent of the present invention has a low concentration of the gelling agent, when it is used as an electrolyte gel, it can increase the content of an organic electrolyte advantageously.

A description is subsequently given of an aromatic compound having a perfluoroalkyl group, represented by the following formula (2) (to be referred to as "aromatic compound (2)" hereinafter), a manufacturing process thereof and use of the aromatic compound as a gelling agent.

The aromatic compound (2) of the present invention is represented by the following formula (2).

$$C_mF_{2m+1}-(CH_2)_q-Z-Ar-O \diagdown_{R^2} \diagup C_mF_{2m+1}-(CH_2)_q-Z-Ar-O \quad (2)$$

In the formula (2), $R^2$ is a saturated or unsaturated divalent hydrocarbon group having 2 to 20 carbon atoms, Ar and m are as defined hereinabove, Z is a sulfur atom or oxygen atom, and q is 0 or an integer of 1 to 4.

In the formula (2), the descriptions and examples of Ar and $C_mF_{2m+1}$ are the same as in the formula (1). A substituent not preferred for (1) the introduction of a perfluoroalkyl(oligomethylene)thio group and (2) the introduction of a hydrocarbon oxy group is not preferred as a substituent for the aromatic compound of the formula (8) having a hydroxyl group and a thiol group.

In the above formula (2), the number of carbon atoms of the oligomethylene group $(CH_2)_q$ may be 0, which means that there may be no oligomethylene group. In the compound of the present invention, the number of carbon atoms of the oligomethylene group $(CH_2)_q$ is 0 to 4. A compound having an oligomethylene group $(CH_2)_q$ with 5 or more carbon atoms has low gelation ability.

In the formula (2), the hydrocarbon group $R^2$ is a saturated or unsaturated divalent hydrocarbon group having 2 to 20 carbon atoms. The hydrocarbon group $R^2$ may be branched or not branched in the case of an aliphatic hydrocarbon. When an aromatic hydrocarbon is contained, a substituent may be existent in the aromatic nucleus. As a matter of course, it may be an arylalkyl group such as benzyl group.

A compound having no hydrocarbon group $R^2$ does not dissolve in an organic liquid and cannot gel an organic liquid. When the hydrocarbon group has 21 or more carbon atoms, it is difficult to acquire raw materials.

The process of manufacturing the aromatic compound (2) of the present invention comprises reacting the aromatic compound of the following formula (8) with a halogenated compound having a perfluoroalkyl group, represented by the following formula (9), reacting the obtained product with an aromatic compound having a hydroxyl group and a perfluoroalkyl group, represented by the following formula (10) and reacting the obtained product with a dihalogenated hydrocarbon represented by the following formula (11).

$$HZ-Ar-OH \quad (8)$$

$$C_mF_{2m+1}-(CH_2)_q-X^2 \quad (9)$$

$$C_mF_{2m+1}-(CH_2)_p-Z-Ar-OH \quad (10)$$

$$X^2-R^2-X^2 \quad (11)$$

(the symbols in the above formulas are as defined in the above formulas (1) and (2), and $X^2$ is a halogen atom reactive to a thiol group or a hydroxyl group.)

The halogen atom $X^2$ in the formula (9) may be reactive to the group ZH (thiol group or hydroxyl group) of the compound (HZ—Ar—OH) of the formula (8), and chlorine, bromine or iodine may be used.

The halogen atom $X^2$ of the dihalogenated hydrocarbon $(X^2-R^2-X^2)$ may be reactive to the hydroxyl group of the compound of the formula (10), and chlorine, bromine or iodine may be used.

Since the gelling agent of the present invention which is composed of the above aromatic compound (2) has totally the same effect, function and use as the gelling agent which is composed of the above aromatic compound (1), the above description is applied herein as it is.

A description is subsequently given of the aromatic compound having a perfluoroalkyl group, represented by the above formula (3) (to be referred to as "aromatic compound (3)" hereinafter), a manufacturing process thereof and use of the aromatic compound as a gelling agent.

The aromatic compound (3) of the present invention is represented by the following formula (3).

$$C_mF_{2m+1}-(CH_2)_q-S-Ar-OR^1 \quad (3)$$

In the above formula, Ar, $R^1$, m and q are as defined hereinabove.

The definitions of Ar, $R^1$ and m in the above formula (3) are the same as in the above formula (1). These descriptions and examples of these are the same as in the above formula (1). The definition of q is the same as in the above formula (2) and its description and examples are the same as in the above formula (2).

The aromatic compound (3) of the present invention can be manufactured by (1) introducing a perfluoroalkyl(oligomethylene)thio group into an aromatic compound having a hydroxyl group and a thiol group (formula (12)) by means of the compound of the above formula (a) and (2) introducing a hydrocarbon oxy group by means of a compound of the following formula (13).

(1) Introduction of Perfluoroalkyl(Oligomethylene)Thio Group

The aromatic compound having a hydroxyl group and a thiol group (formula (12)) is dissolved in a solvent such as tetrahydrofuran (THF) and reacted with the halogenated compound having a perfluoroalkyl(oligomethylene) group (the above formula (9)) in the presence of a base such as amine and neutralized with hydrochloric acid, and the solvent and unreacted substances are distilled off to produce an aromatic compound having a hydroxyl group and a perfluoroalkyl(oligomethylene) group (formula (13)).

$$HS-Ar-OH \quad (12)$$

$$C_mF_{2m+1}-(CH_2)_q-X^2 \quad (9)$$

$$C_mF_{2m+1}-(CH_2)_q-S-Ar-OH \quad (13)$$

$$R^1-X^1 \quad (14)$$

(the meanings of the symbols in the above formulas are the same as in the above formulas, and $X^1$ is a halogen atom reactive to a hydroxyl group.)

(2) Introduction of Hydrocarbon Oxy Group

A halogenated hydrocarbon of the formula (14) and a base are added to a solution obtained by dissolving the aromatic compound having a hydroxyl group and a perfluoroalkyl (oligomethylene) group (formula (13)) in a solvent and refluxed. After the end of a reaction, the resulting solution is filtered as required, the solvent and unreacted substances are distilled off from the reaction solution, and the residue is refined by a silica gel chromatograph to introduce a hydrocarbon oxy group so as to manufacture the aromatic compound having a perfluoroalkyl(oligomethylene)thio group and a hydrocarbon oxy group (formula (3)).

As a matter of course, the process of manufacturing the aromatic compound of the present invention is not limited to the above process.

Since the gelling agent of the present invention which is composed of the above aromatic compound (3) has the same function, effect and use as the gelling agent which is composed of the above aromatic compound (1), the above description is applied herein as it is.

EXAMPLES

The following examples are provided for the purpose of further illustrating the present invention but are in no way to be taken as limiting.

Example 1

The compound (A), the compound (B), the compound (C) and the compound (D) were manufactured in this order according to the following chemical reaction formula (1).

(1) Synthesis of Compound (A)

1.0 equivalent of 4-bromobutene and 1.5 equivalents of potassium carbonate were added to a 3-pentanone solution of 3 g of 4-pentyloxyphenol and refluxed for 2 days. A precipitate separating out from the reaction solution was separated by filtration, the solvent of the filtrate was distilled off, and the residue was refined by silica gel column chromatography to obtain a compound (A) (2 g, 40%).
Oily Substance IR (cm$^{-1}$) ν=823.5, 1039.4, 1230.4, 1508.1, 2931.3.

$^1$HNMR (270 MHz, CDCl$_3$) δ=0.92 (3H, t, J=6.9 Hz), 1.33-1.46 (4H, m), 1.75 (2H, quin, J=6.9 Hz), 2.51 (2H q, J=6.9 Hz), 3.89 (2H, t, J=6.4 Hz), 3.96 (2H, t, J=6.6 Hz), 5.07-5.19 (2H, m), 5.82-5.97 (1H, m), 6.82 (4H, s) ppm (2) Synthesis of Compound (B)

Perfluorooctyl iodide (4.8 g, 8.79 mmol), sodium hydrogen carbonate (0.7 g, 8.69 mmol) and hydrosulfite sodium (1.5 g, 8.79 mmol) were added to an acetonitrile (8.5 ml) and water (5.5 ml) solution of the compound (A) (2.0 g, 8.77 mmol) and stirred under shielded light for one night. After the end of a reaction, the reaction solution was diluted with ethyl acetate and rinsed with water twice and then with a saline solution. After the organic layer was dried with sodium sulfate, the solvent was removed under a reduced pressure. The residue was refined with a chloroform solvent by column chromatography. 2.8 g (41%) oily substance.

IR (KBr, cm$^{-1}$) ν=1149.4, 1203.4, 1234.2 cm$^{-1}$ (C—F), 1511.9 cm$^{-1}$, 2933.2, 2958.3 cm$^{-1}$ (C—H)

$^1$HNMR (270 MHz, CDCl$_3$) δ=0.93 (3H, t, J=6.9 Hz), 1.26-1.48 (4H, m), 1.76 (2H, quin, J=6.9 Hz), 2.14-2.36 (2H, m), 2.84-3.06 (2H, m), 3.91 (2H, t, J=6.6 Hz), 4.00-4.16 (2H, m), 4.56-4.66 (1H, m), 6.84 (4H, s) ppm (3) Synthesis of Compound (C)

The compound (B) (2.8 g, 3.58 mmol) was dissolved in distilled THF (25 ml) without being exposed to the air, and LiAlH$_4$ (0.28 g, 7.37 mmol) was added to the resulting solution and stirred for one night. After the end of a reaction, an aqueous solution of ammonium chloride was added for extraction, and the obtained extract was rinsed with water twice and then with a saline solution. After the organic layer was dried with magnesium sulfate, the solvent was removed under a reduced pressure. The residue was refined with a chloroform solvent by column chromatography to obtain an achromatic solid (C). 1.39 g (60%). mp=57° C.

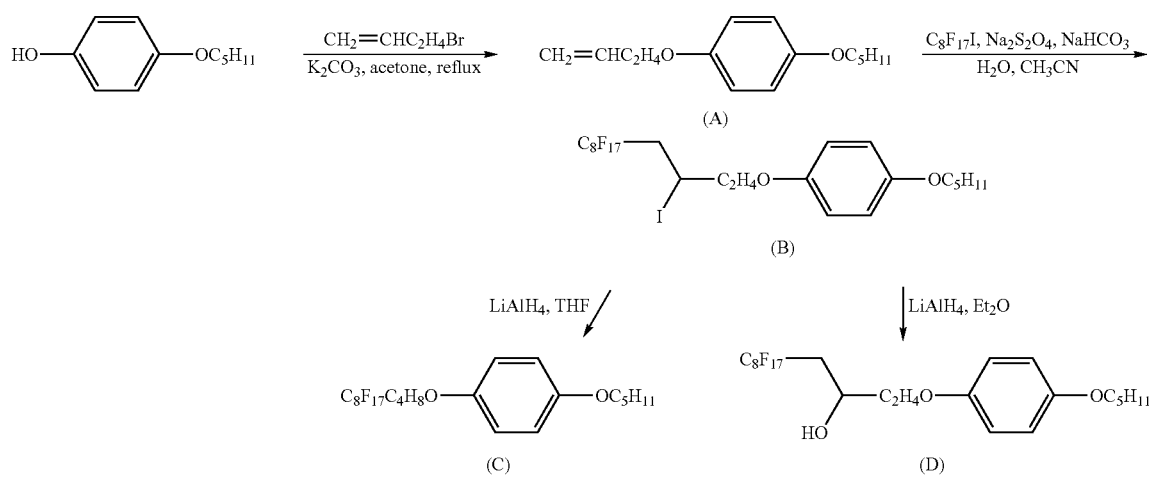

(I)

IR (KBr, cm$^{-1}$) ν=1149.4, 1209.1, 1238.1 cm$^{-1}$ (C—F), 1508.1 cm$^{-1}$, 2873.4, 2913.9, 2952.5 cm$^{-1}$ (C—H)

$^1$HNMR (CDCl$_3$) δ=0.93 (3H, t, J=7.0 Hz), 1.30-1.45 (4H, m), 1.70-1.90 (6H, m), 2.15 (2H, m), 3.90 (2H, t, J=7.0 Hz), 3.92 (2H, t, J=7.0 Hz), 6.82 (4H, s) ppm (4) Synthesis of Compound (D)

A few hours after the compound (B) (1.10 g) was distilled, LiAlH$_4$ (0.1 g) was added to a diethyl ether (20 ml) solution of the compound (B) and stirred for one night. After the end of a reaction, 1N HCl was added for extraction, and the obtained extract was rinsed with water twice and then with a saline solution. After the organic layer was dried with magnesium sulfate, the solvent was removed under a reduced pressure, and the residue was refined with a chloroform solvent by column chromatography to obtain an achromatic solid (D). 0.32 g. mp=92° C.

IR (KBr, cm$^{-1}$) ν=1147.4, 1203.4, 1238.1, 1511.9, 2937.1, 3415.3, 3438.5, 3469.3, 3498.2 cm$^{-1}$ $^1$HNMR (CDCl$_3$) δ=0.93 (3H, t, J=7.1 Hz), 1.34-1.46 (4H, m), 1.76 (2H, quin, J=6.9 Hz), 2.02 (2H, m), 2.20-2.46 (2H, m), 2.70 (1H, d, J=3.3 Hz), 3.90 (2H, t, J=6.6 Hz) 4.07-4.20 (2H, m), 4.46 (1H, m), 6.83 (4H, s) ppm Example 2

The above compound (C) was added to each organic solvent and dissolved in the organic solvent by heating, and the formed solution was returned to normal temperature to observe whether the solvent was gelled or not so as to measure its gelation ability. The organic solvents used in this example were propylene carbonate, methanol, DMF, 1-octanol and acetonitrile. The above compound (C) could gel these organic solvents.

The minimum gelation concentration (wt %) at room temperature of the compound (C) was as follows. Propylene carbonate (2.3), methanol (3.6), DMF (4.6), 1-octanol (14.0) and acetonitrile (20.1)

Example 3

The above compound (D) was added to each organic solvent and dissolved in the organic solvent by heating, and the formed solution was returned to normal temperature to observe whether the solvent was gelled or not so as to measure its gelation ability. The organic solvents used in this example were propylene carbonate, methanol, DMF, 1-octanol, acetonitrile, cyclohexane and octane. The above compound (D) could gel these organic solvents.

The minimum gelation concentration (wt %) at room temperature of the compound (D) was as follows. Propylene carbonate (1.1), cyclohexane (2.1), octane (2.5), methanol (5.2), 1-octanol (5.6), acetonitrile (5.9), N,N-diethyl-N-methyl-N-(2-methoxyethyl)ammonium bis(trifluoromethanesulfonyl)imide (4.7)

The sol-gel transition temperature was as follows when 10 wt % of the gelling agent was added: cyclohexane: 55° C., acetonitrile: 48° C., methanol: 40° C., octane: 60° C., N,N-dimethyl-N-methyl-N-(2-methoxyethyl)ammonium bis(trifluoromethanesulfonyl)imide: 63° C. (addition of 5 wt %)

Example 4

The compound (b) was manufactured from the compound (a) and then the compound (c) was manufactured from the compound (b) according to the following chemical reaction formula.

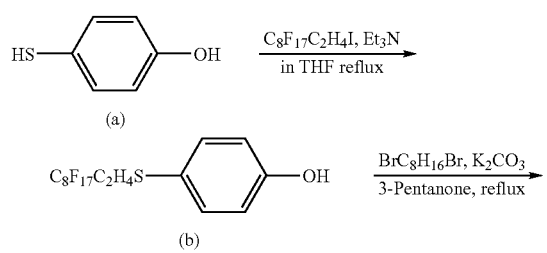

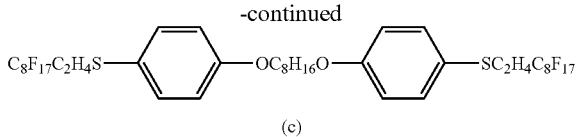

(1) Synthesis of Compound (b)

1.2 equivalents of triethylamine and 1.0 equivalent of C$_8$F$_{17}$C$_2$H$_4$I were added to a THF (tetrahydrofuran) solution of 2 g of the compound (a) and refluxed for 24 hours. Thereafter, 1N hydrochloric acid was added to carry out extraction with ether, and the obtained extract was rinsed with water (twice) and then with a saline solution and dried with magnesium sulfate. The solvent was distilled off, and the residue was refined by silica gel column chromatography to obtain the compound (b) (7.80 g, yield of 87%).

mp=97° C.

IR (KBr, cm$^{-1}$) ν=1145, 1203, 1240 (CF$_2$) cm$^{-1}$, 3400 (O—H) cm$^{-1}$ $^1$HNMR (270 MHz, CDCl$_3$) δ=2.33 (2H, m), 2.99 (2H, m), 5.20 (1H, s), 6.81 (2H, d, J=8.9 Hz), 7.31 (2H, d, J=8.9 Hz) ppm (2) Synthesis of Compound (c)

0.5 equivalent of 1,8-dibromooctane and 1.5 equivalents of potassium carbonate were added to a 3-pentanone solution of 0.5 g of the compound (b) and refluxed for 20 hours. A precipitate separating out from the reaction solution was separated by filtration, the solvent of the filtrate was distilled off under a reduced pressure, and the filtrate was refined by silica gel column chromatography to obtain the compound (c) (0.5 g, 76%).

mp=115° C.

IR (KBr, cm$^{-1}$) ν=1147, 1203, 1245, 1496, 3220 cm$^{-1}$ $^1$HNMR (270 MHz, CDCl$_3$) δ=1.22-1.45 (8H, m), 1.78 (4H, quin, J=6.6 Hz), 2.33 (4H, m), 2.99 (4H, m), 3.94 (4H, t, J=6.8 Hz), 6.86 (4H, d, J=8.9 Hz), 7.36 (4H, d, J=8.9 Hz) ppm Example 5

The above compound (c) was added to each organic solvent and dissolved in the organic solvent by heating, and the formed solution was returned to normal temperature to observe whether the solvent was gelled or not so as to measure its gelation ability. The organic solvents used in this example were propylene carbonate, acetonitrile, DMF, octanol, ethanol, octane and cyclohexane. About 5 wt % or less of the above compound (c) could gel these organic solvents.

The minimum gelation concentration (wt %) at room temperature of the compound (c) was as follows. Acetonitrile (0.9), DMF (1.4), octanol (1.4), ethanol (1.5), octane (1.7), propylene carbonate (2.6), cyclohexane (5.0)

The sol-gel transition temperature was as follows when 10% of the gelling agent was added: cyclohexane: 70° C., 1-octanol: 65° C., acetonitrile: 65° C.

Example 6

The compound (e) was manufactured from the compound (d) and then the compound (f) was manufactured from the compound (e) according to the following chemical reaction formula.

$$HS-\text{[benzene ring]}-OH \xrightarrow[\text{In THF reflux}]{C_8F_{17}C_2H_4I, Et_3N}$$

(d)

$$C_8F_{17}C_2H_4S-\text{[benzene ring]}-OH \xrightarrow[\text{3-Pentanone, reflux}]{C_{13}H_{21}Br, K_2CO_3}$$

(e)

$$C_8F_{17}C_2H_4S-\text{[benzene ring]}-OC_{13}H_{27}$$

(f)

(1) Synthesis of Compound (e)

1.2 equivalents of triethylamine and 1.0 equivalent of $C_8F_{17}C_2H_4I$ were added to a THF (tetrahydrofuran) solution of 2 g of the compound (d) and refluxed for 24 hours. Thereafter, 1N hydrochloric acid was added to carry out extraction with ether, and the obtained extract was rinsed with water (twice) and then with a saline solution and dried with magnesium sulfate. The solvent was distilled off, and the residue was refined by silica gel column chromatography to obtain the compound (e) (7.80 g, yield of 87%). Compound (e); $^1$HNMR (CDCl$_3$) δ=2.33 (2H, m), 2.99 (2H, m), 5.20 (1H, s), 6.81 (2H, d, J=8.9 Hz), 7.31 (2H, d, J=8.9 Hz) ppm.

mp=97° C.

IR (KBr, cm$^{-1}$) ν=1145, 1203, 1240 (CF$_2$) cm$^{-1}$, 3400 (O—H) cm$^{-1}$ (2) Synthesis of Compound (f)

1.0 equivalent of 1-bromotridecane and 1.5 equivalents of potassium carbonate were added to a 3-pentanone solution of 0.5 g of the compound (e) and refluxed for 20 hours. A precipitate separating out from the reaction solution was separated by filtration, the solvent of the filtrate was distilled off, and the filtrate was refined by silica gel column chromatography to obtain the compound (f) (0.5 g, 76%).

mp=63° C.

IR (KBr, cm$^{-1}$)=1147, 1201, 1238, 2918 cm$^{-1}$ $^1$HNMR (270 MHz, CDCl$_3$) δ=0.88 (3H, t, J=6.8 Hz), 1.22-1.45 (20H, m), 1.78 (2H, quin, J=6.6 Hz), 2.33 (2H, m), 2.99 (2H, m), 3.94 (2H, t, J=6.6 Hz), 6.86 (2H, d, J=8.6 Hz), 7.36 (2H, d, J=8.6 Hz) ppm

Example 7

The above compound (f) was added to each organic solvent and dissolved in the organic solvent by heating, and the formed solution was returned to normal temperature to observe whether the solvent was gelled or not so as to measure its gelation ability. The organic solvents used in this example were propylene carbonate, methanol, octanol, acetonitrile, DMF, octane and cyclohexane. About 5 wt % or less of the above compound (f) could gel these organic solvents.

The minimum gelation concentration (wt %) at room temperature of the compound (f) was as follows. DMF (0.79), methanol (0.90), acetonitrile (1.3), 1-octanol (3.0), propylene carbonate (0.9), cyclohexane (2.8), octane (5.2), N,N-diethyl-N-methyl-N-(2-methoxyethyl)ammonium tetrafluoroborate (5.0)

The physical properties of this gel were measured by the following methods.

(i) Deformation Rate, Gel Strength, Hardness

The deformation rate A (%) of a gel and the force B (g/cm$^2$) at the time of the degradation of the gel were measured by installing a glass tube having an inner diameter of 15 mm upright, forming a gel to a height of 15 mm in the tube and pressuring it with a disk having a diameter of 10 mm from above. The measurement results are as follows.

Deformation rate A: 33.0%
Gel strength B: 9.9 g/cm$^2$
Hardness B/A: 30.9 g/cm$^2$ (ii) Ion Conductivity The ion conductivity was measured under the following conditions.

Solvent: ethylene carbonate:dimethyl carbonate (volume rate: 1:1)
Electrolyte: LiBF$_4$ (0.5 mol/l)
Temperature: 24° C.
Result: 5.57×10$^{-3}$ Scm$^{-1}$ (gelling agent=2.85 wt %)

The ion conductivity of a blank (without a gelling agent) was 6.76×10$^{-3}$ cm$^{-1}$.

The invention claimed is:

1. An aromatic compound having a perfluoroalkyl group, represented by the following formulas (2) or (3):

$$\begin{array}{l} C_mF_{2m+1}-(CH_2)_q-Z-Ar-O \\ \phantom{C_mF_{2m+1}-(CH_2)_q-Z-Ar-O}\diagdown \\ \phantom{C_mF_{2m+1}-(CH_2)_q-Z-Ar-O\diagdown}R^2 \\ \phantom{C_mF_{2m+1}-(CH_2)_q-Z-Ar-O}\diagup \\ C_mF_{2m+1}-(CH_2)_q-Z-Ar-O \end{array} \quad (2)$$

wherein R$^2$ is a saturated or unsaturated divalent hydrocarbon group having 2 to 20 carbon atoms, Ar is a divalent aromatic group having 5 to 30 aromatic nuclear atoms which aromatic group is optionally substituted by at least one substituent selected from the group consisting of an alkyl group and a halogen atom, Z is a sulfur atom or oxygen atom, m is a natural number of 6 to 12, and q is 0 or an integer of 1 to 4, $$C_mF_{2m+1}-(CH_2)_q-S-Ar-OR^1 \quad (3)$$

wherein R$^1$ is a saturated or unsaturated monovalent hydrocarbon group having 5 to 13 carbon atoms, and Ar, m and q are as defined hereinabove.

2. The aromatic compound according to claim 1, wherein Ar in the formulas (2) and (3) is a phenylene group, biphenylene group or naphthylene group.

3. A process of manufacturing an aromatic compound having a perfluoroalkyl group, represented by formula (1)

$$C_mF_{2m+1}-CH_2-\underset{\alpha}{CH}-(CH_2)_p-O-Ar-OR^1 \quad (1)$$

wherein α is a hydrogen atom or hydroxyl group, Ar is a divalent aromatic group having 5 to 30 aromatic nuclear atoms which aromatic group is optionally substituted by at least one substituent selected from the group consisting of an alkyl group and a halogen atom, R$^1$ is a saturated or unsaturated monovalent hydrocarbon group having 1 to 20 carbon atoms, m is a natural number of 6 to 12, and p is a natural number of 1 to 4, comprising the steps of:

1) reacting an aromatic compound represented by the following formula (4):

$$HO-Ar-OR^1 \quad (4)$$

wherein Ar and R¹ are as defined in the above formula (1), with a halogenated alkene represented by the following formula (5):

wherein p is as defined in the above formula (1), and X¹ is a halogen atom reactive with a hydroxyl group;

2) reacting the obtained product with a perfluoroalkyl iodide represented by the following formula (6):

wherein m is as defined in the above formula (1); and 3) converting the iodine atom of the obtained product represented by the following formula (7) into a hydrogen atom or hydroxyl group:

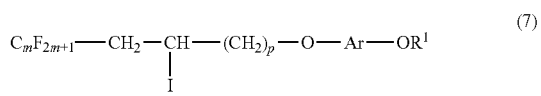

wherein Ar, R¹, m and p are as defined in the above formula (1).

4. A process of manufacturing an aromatic compound having a perfluoroalkyl group, represented by formula (2),

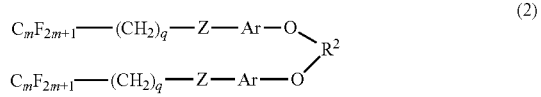

wherein $R^2$ is a saturated or unsaturated divalent hydrocarbon group having 2 to 20 carbon atoms, Ar is a divalent aromatic group having 5 to 30 aromatic nuclear atoms which aromatic group is optionally substituted by at least one substituent selected from the group consisting of an alkyl group and a halogen atom, m is a natural number of 6 to 12, Z is a sulfur atom or oxygen atom, and q is 0 or an integer of 1 to 4, comprising the steps of:

1) reacting an aromatic compound represented by the following formula (8):

HO—Ar—ZH      (8)

wherein Ar and Z are as defined in the above formula (2), with a halogenated compound having a perfluoroalkyl group, represented by the following formula (9):

wherein m and q are as defined in the above formula (2), and $X^2$ is a halogen atom reactive with a thiol group or hydroxyl group;

2) reacting the obtained product with a hydroxyl compound having a perfluoroalkyl group, represented by the following formula (10):

wherein Z, Ar, m and q are as defined in the above formula (2); and 3) reacting the obtained product with a dihalogenated hydrocarbon represented by the following formula (11):

$X^2$—$R^2$—$X^2$      (11)

wherein $R^2$ is as defined in the above formula (2), and $X^2$ is as defined in the above formula (9).

5. A process of manufacturing an aromatic compound having a perfluoroalkyl group, represented by formula (3)

wherein Ar is a divalent aromatic group having 5 to 30 aromatic nuclear atoms which aromatic group is optionally substituted by at least one substituent selected from the group consisting of an alkyl group and a halogen atom, $R^1$ is a saturated or unsaturated monovalent hydrocarbon group having 1 to 20 carbon atoms, m is a natural number of 6 to 12, and q is 0 or an integer of 1 to 4, comprising the steps of:

1) reacting an aromatic compound represented by the following formula (12):

HO—Ar—SH      (12)

wherein Ar is as defined in the above formula (3), with a halogenated compound having a perfluoroalkyl group, represented by the above formula (9); and 2) reacting the obtained product (13) with a halogenated hydrocarbon represented by the following formula (14):

$R^1$—$X^1$      (14)

wherein $R^1$ is as defined in the above formula (3), and $X^1$ is as defined in the above formula (5).

6. A gelling agent for gelling an organic liquid, which comprises the aromatic compound having a perfluoroalkyl group, represented by the following formulas (2) or (3):

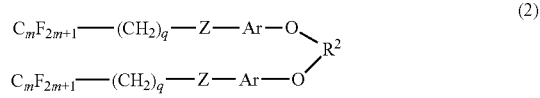

wherein $R^2$ is a saturated or unsaturated divalent hydrocarbon group having 2 to 20 carbon atoms, atoms, Ar is a divalent aromatic group having 5 to 30 aromatic nuclear atoms which aromatic group is optionally substituted by at least one substituent selected from the group consisting of an alkyl group and a halogen atom, Z is a sulfur atom or oxygen atom, m is a natural number of 6 to 12, and q is 0 or an integer of 1 to 4,

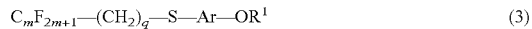

wherein $R^1$ a saturated or unsaturated monovalent hydrocarbon group having 5 to 13 carbon atoms, and Ar, $R^1$, m and q are as defined hereinabove.

7. A gel formed by gelling an organic liquid with the gelling agent of claim 6.

8. The gel according to claim 7, wherein the organic liquid is an electrolyte and the gel is an electrolyte.

9. The aromatic compound according to claim 1, wherein Ar is unsubstituted.

\* \* \* \* \*